(12) United States Patent
van der Bruggen et al.

(10) Patent No.: US 6,194,156 B1
(45) Date of Patent: Feb. 27, 2001

(54) ISOLATED NUCLEIC ACID MOLECULES WHICH ENCODE TAGE MOLECULES, AND USES THEREOF

(75) Inventors: Pierre van der Bruggen; Thierry Boon-Falleur, both of Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/324,231

(22) Filed: Jun. 2, 1999

Related U.S. Application Data

(62) Division of application No. 09/160,845, filed on Sep. 25, 1998, now Pat. No. 5,952,468, which is a division of application No. 09/036,467, filed on Mar. 6, 1998, now Pat. No. 5,905,145.

(51) Int. Cl.$^7$ .............................. C12Q 1/68; C07H 21/04; C12N 15/11
(52) U.S. Cl. .............................. 435/6; 536/23.1; 536/24.3; 536/24.31; 536/24.33; 435/91.1; 435/91.2
(58) Field of Search ................................ 435/6, 7.21, 7.23, 435/91.2, 91.1; 536/23.1, 24.3, 24.31, 24.33

(56) References Cited

U.S. PATENT DOCUMENTS

| | | | |
|---|---|---|---|
| 5,905,145 | * | 5/1999 | Van Der Bruggen et al. ..... 536/23.1 |
| 5,952,468 | * | 9/1999 | Van Der Bruggen et al. ..... 530/350 |

* cited by examiner

*Primary Examiner*—David Guzo
*Assistant Examiner*—Jon Shuman
(74) *Attorney, Agent, or Firm*—Fulbright & Jaworski, LLP

(57) ABSTRACT

A new family of tumor rejection antigen precursors, and the nucleic acid molecules which code for them, are disclosed. These tumor rejection antigen precursors are referred to as TAGE tumor rejection antigen precursors, and the nucleic acid molecules which code for them are referred to as TAGE coding molecules. Various diagnostic and therapeutic uses of the coding sequences and the tumor rejection antigens, and their precursor molecules are described.

10 Claims, No Drawings

ISOLATED NUCLEIC ACID MOLECULES WHICH ENCODE TAGE MOLECULES, AND USES THEREOF

This application is a divisional of Ser. No. 09/160,845, filed Sep. 25, 1998, now U.S. Pat. No. 5,962,468, which is a division of Ser. No. 09/036,467 filed on Mar. 6, 1998, now U.S. Pat. No. 5,905,145.

FIELD OF THE INVENTION

This invention relates to a family of nucleic acid molecules which code for a tumor rejection antigen precursor. The tumor rejection antigen precursor, or "TRAP" may be processed into peptides presented by human leukocyte antigen molecules. The genes in question do not appear to be related to other known tumor rejection antigen precursor coding sequences.

BACKGROUND AND PRIOR ART

The process by which the mammalian immune system recognizes and reacts to foreign or alien materials is a complex one. An important facet of the system is the T lymphocyte, or "T cell" response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J. P. Lipincott Company, 1987), especially chapters 6–10. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific cytolytic T lymphocytes, or "CTLs" hereafter. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. patent application Ser. No. 807,043, filed Dec. 12, 1991, now U.S. Pat. No. 5,342,774, incorporated by reference in its entirety. The "MAGE" family of tumor rejection antigen precursors is disclosed in this patent.

In U.S. Pat. No. 5,405,940, the disclosure of which is incorporated by reference, it is explained that the MAGE-1 gene codes for a tumor rejection antigen precursor which is processed to nonapeptides which are presented by the HLA-A1 molecule. The nonapeptides which bind to HLA-A1 follow a "rule" for binding in that a motif is satisfied. In this regard, see e.g. PCT/US93/07421; Falk et al., Nature 351: 290–296 (1991); Engelhard, Ann Rev. Immunol. 12: 181–207 (1994); Ruppert et al., Cell 74: 929–937 (1993); Rotzschke et al., Nature 348: 252–254 (1990); Bjorknan et al., Nature 329: 512–518 (1987); Traversari et al., J. Exp. Med. 176: 1453–1457 (1992). The reference teaches that given the known specificity of particular peptides for particular HLA molecules, one should expect a particular peptide to bind to one HLA molecule, but not to others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 now U.S. Pat. No. 5,558,995 and incorporated by reference, the fact that the MAGE-1 expression product is processed to a second TRA is disclosed. This second TRA is presented by HLA-Cw 1601 molecules. The disclosure shows that a given TRAP can yield a plurality of TRAs, each of which will satisfy a motif rule for binding to an MHC molecule.

In U.S. patent application Ser. No. 994,928, filed Dec. 22, 1992, now abandoned and incorporated by reference herein teaches that tyrosinase, a molecule which is produced by some normal cells (e.g., melanocytes), is processed in tumor cells to yield peptides presented by HLA-A2 molecules.

In U.S. Pat. No. 5,683,886 and incorporated by reference in its entirety, a second TRA, not derived from tyrosinase is taught to be presented by HLA-A2 molecules. This TRA is derived from a TRAP, but is coded for by a non-MAGE gene. This disclosure shows that a particular HLA molecule may present TRAs derived from different sources.

In U.S. Pat. No. 5,571,711, filed Jun. 17, 1993 and incorporated by reference herein, an unrelated tumor rejection antigen precursor, the so-called "BAGE" precursor is described. The BAGE precursor is not related to the MAGE family.

In U.S. patent applications Ser. No. 08/096,039, now abandoned, and Ser. No. 08/250,162, now U.S. Pat. No. 5,660,013 both of which are incorporated by reference, non-related TRAP precursor GAGE is also disclosed.

The work which is presented by the papers, patent, and patent applications cited supra deals, in large part, with the MAGE family of genes, and the unrelated BAGE and GAGE genes. It has now been found, however, that additional tumor rejection antigen precursors are expressed by cells. These tumor rejection antigen precursors are referred to as "TAGE" tumor rejection antigen precursors. They do not show homology to the MAGE family of genes, the BAGE family of genes, or the GAGE family of genes. Thus the present invention relates to genes encoding such TAGE TRAPs, the encoded tumor rejection antigen precursors, tumor rejection antigens derived therefrom, fragments of the gene, as well as uses of these.

The invention is elaborated upon further in the disclosure which follows.

DETAILED DESCRIPTION OF PREFERRED EMBODIMENTS

Example 1

This example describes the isolation of a nucleic acid molecule in accordance with this invention.

A cDNA library was prepared from testis tissues, following standard methodologies. Specifically, poly A RNA was isolated, using a commercially available, oligo-dT mRNA extraction kit. Once the RNA was isolated, it was converted to cDNA, using oligo-dT primers and standard methods.

The cDNA was then ligated to NotI/BstX adaptors, inserted into known expression vector pcDNAI/Amp, and the resulting recombinant plasmids were electroporated into E. coli DH5αF'IQ. The transfected bacteria were then selected with ampicillin (50 ug/ml), plated onto nylon based membranes, and duplicated, following Sambrook et al., Molecular Cloning: A Laboratory Manual (Cold Spring Harbor Laboratory Press, 1989), p. 1.94, incorporated by reference. In brief, bacteria are plated onto a membrane, which is then placed on a solid medium and, when colonies are visible, a second membrane is laid down on the first. Some bacterial stick to the second membrane, thus creating a duplicate.

Following pretreatment, the membranes were then used in hybridization experiments. Specifically, these were contacted with a solution of 10% dextran sulfate, 1% SDS, and 1M NaCl, at 65° C., with a $^{32}$P labelled oligonucleotide probe. The probe consisted of nucleotides 100–385 of SEQ ID NO: 1 of U.S. Pat. No. 5,571,711, incorporated by reference, followed by two, five minute room temperature washes, (2xSSC), followed by two, thirty minute washes at 2xSSC, 1% SDS, at 60° C.

One of the positive clones was partially sequenced. The 482 base pair partial sequence is set forth as SEQ ID NO: 1. It showed no homology with known sequences, nor with the sequence of the cDNA from which the hybridization probe was derived. Hybridization did occur, due to the low stringency conditions.

Example 2

Experiments were then carried out to determine if the isolated nucleic acid molecule referred to as "TAGE" hereafter, belonged to a family of genes. To do this, genomic DNA from melanoma cell line MZ2-MEL (described in U.S. Pat. No. 5,342,774, incorporated by reference), was digested with EcoRI. A nucleotide probe based upon SEQ ID NO: 1 was prepared, which consisted of nucleotides 166–446 of SEQ ID NO: 1, and used in Southern blotting of the genomic digest. Stringent conditions were used (0.2xSSC1% SDS, 20 minutes at 60° C.) and two bands of 3.5 and 6.5 kb, respectively, were observed. The experiments were repeated, using a Hind III digest, and 4 bands were observed. Two of the bands were larger than 12 kb, and the other two were 5 and 7 kilobases long. These results indicate that there is probably a family of TAGE genes.

Example 3

Studies were then carried out to determine whether TAGE genes were expressed in normal or cancerous cells and tissues. To do this, total RNA was extracted from samples using standard guanidine isothiocyanate procedures. Reverse transcription was carried out on 2 ug of RNA using oligodT primers, to secure cDNA. An amount of cDNA corresponding to 100 ng of total RNA ($10^4$ cells), was then amplified via PCR, for 30 cycles, preceded by treatment at 94° C. for five minutes, and 73° C. for 15 minutes. One cycle was defined as one minute at 94° C., two minutes at 59° C., and two minutes at 73° C. The primers consisted of nucleotides 166–187 and the complement to nucleotides 425–446 of SEQ ID NO: 1, respectively. The expected PCR product is 281 base pairs long.

Following amplification, products were size fractionated on a 1.5% agarose gel. PCR amplification of human β-actin was used as a control.

Of the 20 normal adult tissue types tested, only sperm and testis were positive. None of the six fetal tissues tested were positive. Of 22 tumor types tested, strong expression was found in seminoma (100% of samples tested), and expression was also found in melanoma, sarcoma, head and neck squamous cell carcinoma and neuroblastoma. Fifteen types of tumor cell lines were tested, and sarcoma, neuroblastoma, pleural mesothelioma, and thyroid carcinoma cell lines were positive.

The foregoing examples show the isolation of a nucleic acid molecule which codes for a tumor rejection antigen precursor. This "TRAP" coding molecule, however, was not found to be homologous with any of the previously disclosed MAGE, BAGE or GAGE coding sequences described in the references set forth supra, or with any other known gene. Hence, one aspect of the invention is an isolated nucleic acid molecule having the nucleotide sequence set forth in SEQ ID NO: 1 as well as those fragments or portions of SEQ ID NO: 1 which code for TRAs, i.e., what are sometimes referred to as "minigenes", as well as fragments or portions of these nucleic acid molecules which encode immunologically active portions of TAGE proteins. This sequence is not a MAGE, BAGE or GAGE coding sequence, as will be seen by comparing it to the sequence of any of these genes as described in the cited references. Also a part of the invention are those nucleic acid sequences which code for a tumor rejection antigen precursor and which hybridize to the nucleic acid molecule having the nucleotide sequence of SEQ ID NO: 1 under stringent conditions. The term "stringent conditions" as used herein refers to parameters with which the art is familiar. More specifically, stringent conditions, as used herein, refers to hybridization in 3.5xSSC, 1xDenhardt (0.02% Ficoll, 0.02% polyvinylpyrrolidone, 0.02% BDA), 25 mM NaH$_2$PO$_4$, pH 7.0 , 0.5% SDS, 2 mM EDTA, followed by two, 15 minute washes at 2xSSC, 0.5% SDS at 65° C., followed by a single 15 minute wash at 0.2xSSC, 0.1% SDS at 65° C. There are other conditions, reagents, and so forth which can be used, which result in the same or a higher degree of stringency. The skilled artisan will be familiar with such conditions, and, thus, they are not given here.

It will also be seen from the examples that the invention embraces the use of the sequences in expression vectors, which may be used to transform or to transfect host cells and cell lines, be these prokaryotic (e.g., E. coli), or eukaryotic (e.g., CHO or COS cells). The expression vectors require that the pertinent sequence, i.e., those described supra, be operably linked to a promoter. As it has been found that human leukocyte antigens present tumor rejection antigens derived from tumor rejection antigen precursors, the expression vector may also include a nucleic acid sequence coding for an HLA molecule. In a situation where the vector contains both coding sequences, it can be used to transform or transfect a cell which does not normally express either one. The tumor rejection antigen precursor coding sequence may be used alone, when, e.g., the host cell already expresses HLA molecules. Of course, there is no limit on the particular host cell which can be used. As the vectors contain the two coding sequences, they may be used in host cells which do not express HLAs.

The invention also embraces so called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

To distinguish the nucleic acid molecules and the TRAPs of the invention from the previously described MAGE, BAGE and GAGE materials, the invention shall be referred to as the TAGE family of genes and TRAPs. Hence, whenever "TAGE" is used herein, it refers to the tumor rejection antigen precursors coded for by the sequences described herein. "TAGE coding molecule" and similar terms, are used to describe the nucleic acid molecules themselves.

The invention as described herein has a number of uses, some of which are described herein. First, the invention permits the artisan to diagnose a disorder characterized by expression of the TRAP. These methods involve determining expression of the TRAP gene, and/or TRAs derived therefrom, such as a TRA presented by an HLA. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred. An alternate method for determination is a TNF or $^{51}$Cr release assay, of the types described supra.

The isolation of the TRAP gene also makes it possible to isolate the TRAP molecule itself, especially TRAP molecules containing the amino acid sequence coded for by SEQ ID NO: 1. These isolated molecules when presented as the TRA, or as complexes of TRA and HLA, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to provide a CTL response, or can be cells which express both molecules without transfection. Further, the TRAP molecule, its associated TRAs, as well as complexes of TRA and HLA, may be used to produce antibodies or CTLs, using standard techniques well known to the art. Such vaccines may include one or more cytokines, such as GM-CSF.

When "disorder" is used herein, it refers to any pathological condition where the tumor rejection antigen precursor is expressed and processed. An example of such a disorder is cancer, melanoma in particular. Melanoma is well known as a cancer of pigment producing cells.

Therapeutic approaches based upon the disclosure are premised on a response by a subject's immune system, leading to lysis of TRA presenting cells. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Riddel et al., Science 257: 238 (Jul. 10, 1992); Lynch et al., Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex, where the complex contains the pertinent HLA molecule. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a TAGE sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a TAGE derived, tumor rejection antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus, an adenovirus, a retrovirus, a Yersinia virus, or Ty virus like particles, as described by Layton et al., Immunology 87(2): 171–178 (1996), Gilbert, et al., Nat. Biotechnol. 15(12): 1280–1284 (1997) incorporated by reference, or the bacteria BCG, and the materials de facto "infect" host cells. Other types of carriers, such as liposomes, or cationic lipids may also be used. The cells which result present the complex of interest, and are recognized by autologous CTLs, which then proliferate. A similar effect can be achieved by combining the tumor rejection antigen or the precursor itself with an adjuvant to facilitate incorporation into HLA presenting cells which then present the HLA/peptide complex of interest. The TRAP is processed to yield the peptide partner of the HLA molecule while the TRA is presented without the need for further processing.

Other aspects of the invention will be clear to the skilled artisan and need not be repeated here.

The terms and expressions which have been employed are used as terms of description and not of limitation, and there is no intention in the use of such terms and expression of excluding any equivalents of the features shown and described or portions thereof, it being recognized that various modifications are possible within the scope of the invention.

SEQUENCE LISTING (1) GENERAL INFORMATION:

(iii) NUMBER OF SEQUENCES:  1

(2) INFORMATION FOR SEQ ID NO: 1:

(i) SEQUENCE CHARACTERISTICS:
        (A) LENGTH:   482 base pairs
        (B) TYPE:  nucleic acid
        (C) STRANDEDNESS:  single
        (D) TOPOLOGY:  linear (xi) SEQUENCE DESCRIPTION:  SEQ ID NO: 1:

| | | | | | | |
|---|---|---|---|---|---|---|
| GACAGAGTGT | GCAGCACGAC | CAGAGTGGCT | TTTCTGGCTT | TGCCGCCCAG | CTGCTCCATG | 60 |
| CCAGGAGGAG | GAGGAGACAC | CTAGAGCCTG | CGACACCATG | GCTCGCCTCG | CTGCAGTGTA | 120 |
| GGTTCTACCC | ATGTAACAGA | TGAGGAAACC | AAGGAGCACA | GTTATTTACT | AACTCGCACA | 180 |
| AGGTTCGAGG | CCGAGCTCAG | ACCTGTGGAG | CAGAAGCTGA | GTGCGCTGCA | GTCCCCGCTG | 240 |
| GCCCAGAGGC | CCTTCTTCGA | GGTGCCCTCA | CCCCTGGGCG | CCGTGGACCT | GTACGAGTAT | 300 |
| GCATGCGGGG | ATGAGGACCT | GGAGCCACTG | TGACGCCACC | CATGAGAACG | CCGCTGCGGG | 360 |
| GCCGCTCCAC | ACGTGCCACG | GCCACCACTG | GGACACCGCC | GCTTGTGTAA | AAACTGTTGT | 420 |
| CTTTTGTGGA | AAATGAGTGT | GTTTGCATGG | AATGATAAAT | TTTATTTATT | CACAAAAAAA | 480 |
| AA | | | | | | 482 |

We claim:

1. A method for screening for possible presence of a disorder, comprising assaying a nucleic acid molecule containing sample taken from a subject believed to be afflicted with said disorder for expression of a nucleic acid molecule which encodes a TAGE tumor rejection antigen precursor, the complementary sequence of which hybridizes, under stringent conditions, to SEQ ID NO: 1, wherein expression of said nucleic acid molecule is indicative of possible presence of said disorder.

2. The method of claim 1, comprising polymerase chain reaction.

3. The method of claim 1, comprising contacting said sample with a labelled oligonucleotide probe which hybridizes specifically to an RNA molecule corresponding to a gene which encodes said TAGE tumor rejection antigen precursor.

4. The method of claim 1, wherein said TAGE tumor rejection antigen precursor is the TAGE tumor rejection antigen precursor encoded by the nucleotide sequence set forth in SEQ ID NO: 1.

5. The method of claim 1, further comprising reverse transcribing RNA corresponding to a gene which encodes said TAGE tumor rejection antigen precursor to cDNA, and identifying said cDNA.

6. The method of claim 1, comprising identifying said TAGE tumor rejection antigen precursor protein.

7. The method of claim 1, wherein said disorder is cancer.

8. The method of claim 5, wherein said cDNA comprises the nucleotide sequence set forth in SEQ ID NO: 1.

9. The method of claim 6, wherein said TAGE tumor rejection antigen precursor protein has the amino acid sequence of the TAGE tumor rejection antigen precursor protein encoded by the nucleotide sequence set forth in SEQ ID NO: 1.

10. The method of claim 7, wherein said cancer is seminoma, melanoma, sarcoma, head and neck squamous cell carcinoma, neuroblastoma, mesothelioma, or thyroid carcinoma.

* * * * *